United States Patent [19]

Shaw

[11] Patent Number: 5,632,733

[45] Date of Patent: May 27, 1997

[54] TAMPERPROOF RETRACTABLE SYRINGE

[76] Inventor: Thomas J. Shaw, 1510 Hillcrest, Little Elm, Tex. 75068

[21] Appl. No.: 537,242

[22] Filed: Sep. 29, 1995

Related U.S. Application Data

[63] Continuation-in-part of Ser. No. 438,954, May 11, 1995.

[51] Int. Cl.$^6$ ............................................... A61M 5/00
[52] U.S. Cl. ................................... 604/195; 604/110
[58] Field of Search ................................. 604/195, 192, 604/110, 187, 198, 263

[56] References Cited

U.S. PATENT DOCUMENTS

| | | |
|---|---|---|
| 4,747,831 | 5/1988 | Kulli . |
| 4,838,863 | 6/1989 | Allard et al. . |
| 4,838,869 | 6/1989 | Allard et al. . |
| 4,874,382 | 10/1989 | Lindemann et al. . |
| 4,904,242 | 2/1990 | Kulli . |
| 4,955,870 | 9/1990 | Ridderheim et al. . |
| 4,994,034 | 2/1991 | Botich et al. . |
| 5,019,044 | 5/1991 | Tsao . |
| 5,046,508 | 9/1991 | Weissler . |
| 5,049,133 | 9/1991 | Villen Pascual . |
| 5,053,010 | 10/1991 | McGary et al. . |
| 5,064,419 | 11/1991 | Gaarde . |
| 5,084,018 | 1/1992 | Tsao . |
| 5,084,029 | 1/1992 | Tagliaferri et al. . |
| 5,092,853 | 3/1992 | Gouvertier, II . |
| 5,112,316 | 5/1992 | Venturini ............... 604/195 |
| 5,114,410 | 5/1992 | Caralt Batlle ........... 604/195 |
| 5,118,599 | 6/1992 | Botich et al. . |
| 5,180,369 | 1/1993 | Dysarz . |
| 5,201,710 | 4/1993 | Caselli ................... 604/110 |
| 5,211,629 | 5/1993 | Pressly et al. ........... 604/110 |
| 5,304,138 | 4/1994 | Mercado . |
| 5,324,265 | 6/1994 | Murray . |
| 5,370,620 | 12/1994 | Shonfeld . |
| 5,385,551 | 1/1995 | Shaw . |
| 5,389,076 | 2/1995 | Shaw . |

FOREIGN PATENT DOCUMENTS

| | | |
|---|---|---|
| 146773 | of 1990 | Japan . |
| GB2197792 | 6/1988 | United Kingdom . |

OTHER PUBLICATIONS

Designer's Corner, *Design News*, Mar. 22, 1993.

*Primary Examiner*—John D. Yasko
*Attorney, Agent, or Firm*—Harris, Tucker & Hardin, P.C.

[57] ABSTRACT

A tamperproof retractable non-reusable syringe has a one piece hollow outer body with a barrel for a slidable plunger, a transition zone and a smaller diameter nose portion. An elongated needle holder and spring combination is installable from the rear of the outer body, guided into the nose portion and held by cooperating inwardly and outwardly facing surfaces oriented in the direction of retraction at the most constricted part of the transition zone where the nose begins. The plunger has an opening with a dislodgable stopper for receiving parts of the retraction mechanism. The stopper and the head of the needle holder are of significantly reduced diameter from the injection fluid chamber to resist blowing out prematurely. In one embodiment the head of the needle holder is surrounded by a separable retainer member which is slidingly removed by contact with the tip of the plunger after the stopper is mostly or fully removed to avoid cumulation of force required for retraction after the injection. In a second embodiment the head of the needle holder is clamped and held by constricting forces imposed by stress on the outer body induced by interference fit. Release occurs by slight expansion on the barrel by contact of the plunger tip with a small internal ramp in the outer barrel. Both embodiments have a plunger cap configured to enter an opening in the outer body to provide an additional tamperproof feature.

36 Claims, 5 Drawing Sheets

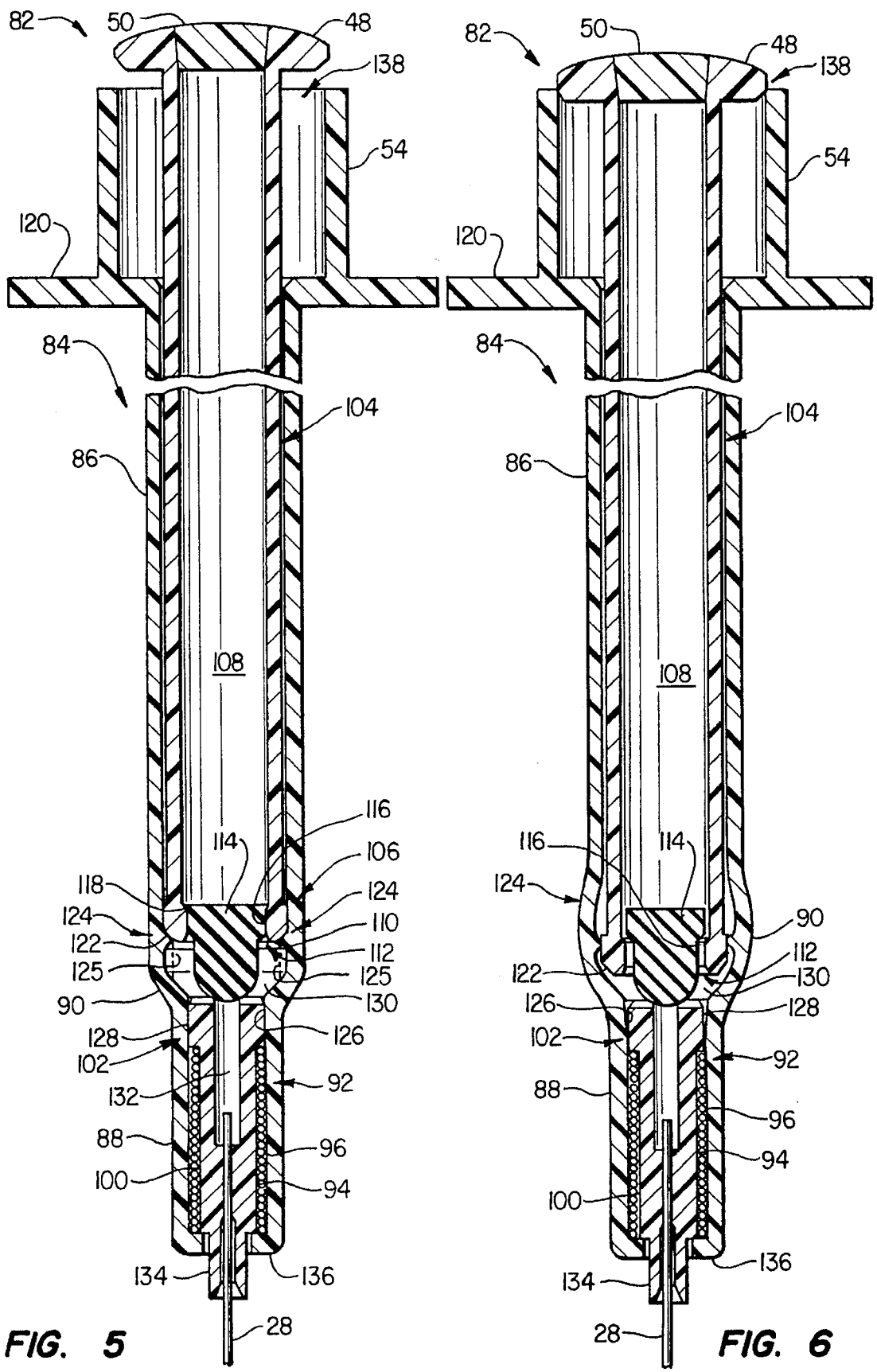

TAMPERPROOF RETRACTABLE SYRINGE

CROSS REFERENCE TO RELATED APPLICATION

This application is a continuation-in-part of copending patent application Ser. No. 08/438,954 filed May 11, 1995 by the same inventor entitled Tamperproof Retractable Syringe for which benefit is claimed under 35 U.S.C. §120.

FIELD OF THE INVENTION

This invention relates to a medical device, and more particularly to a retractable syringe suitable for mass production and assembly having a low triggering force and high blowout pressure which is nonreusable after one use.

BACKGROUND OF THE ART

A major cause to the spread of AIDS in the general population is the presence of IV drug users who share and reuse hypodermic syringes to inject drugs. Infection can be spread from AIDS patients in hospitals and medical facilities through accidental needle sticks from needles used on infected patients. Used syringes with extended needles present a risk to medical personnel and sanitation employees and others in the disposal chain.

The gravity of the threat posed by AIDS and the fact that the main vector of the spread of the dreaded disease is through reuse of syringes by IV drug users has resulted in intense activity to develop the most practical, most reliable, easily assemblable, mass-producible syringe.

There are a number of syringes of different designs which have needles which will retract at the end of the injection cycle. Most of these have never reached the market because of various deficiencies. Prime among the usual deficiencies of the prior art are problems of complexity, reliability, cost and ease of use. The most commonly used syringes are 1 cc and 3 cc syringes which must be mass-produced at the rate of millions per day. Cost is a significant factor both in manufacture of the parts and assembly of the device. High speed production requires molds with 64 cavities or more to reduce unit cycle time. Therefore, molded structures within the barrel that require collapsing core pins such as are shown in much of the art are unlikely to be producible at competitive costs.

One of the problems of the prior art of retractable syringes is the sheer number and complexity of parts which must be formed and assembled. Other problems with the prior art are dependence on flexing or breaking of internal parts by the plunger in order to release the retraction mechanism and use of a diaphragm at the end of the plunger which must be penetrated by a needle holding member and spring. These structures present serious quality control and assembly problems. Small broken off pieces can present a risk of hang-ups. Hooks are often used to releaseably secure retraction mechanisms. Hooks present difficult holding and control problems, may cause retention of air bubbles upon filling and may be undesirably temperature sensitive.

The prior art frequently has a two-piece barrel in order to be able to assemble a retraction device in the nose. This requires at least an additional part and assembly step. It is still necessary to pass the sharp injection needle through a small opening often while compressing a spring before the two parts can be assembled. The tiny needles are produced in the form of coil tubing and vary significantly from straightness after they are cut to length. This leads to difficult assembly problems if the needle must be passed through a small opening. The extremely sharp tip will catch the edge of a hole and jam the production line.

The rare prior art that employs a front mounted retraction mechanism in a one-piece barrel with a plugged hollow plunger, Tsao U.S. Pat. No. 5,084,018, among other things does not show reduced barrel area to prevent excessive blowout pressure, employs engaging flanges to secure all retraction parts, requires concurrent distortion of internal parts and flanges to effect release, cumulating in excessive force required to retract and requires ventilation holes because of a compartmented barrel.

The prior art has not produced a retractable nonreusable tamperproof syringe for mass production and assembly which is simple, reliable, cost effective, easy to use and retract, looks like a conventional syringe, has few parts which are easy to make and assemble, is not temperature sensitive and not subject to danger of premature retraction.

The prior art has not recognized a retraction mechanism with separable parts that relies entirely on clamping force or friction at a smooth walled reduced diameter transition zone in the barrel with mating lands which are slidably or separably released in response to relatively low thumb pressure while having resistance to premature retraction and high blowout pressure resulting from high pressure produced in the fluid chamber during an injection. The prior art has not recognized that such a structure can be molded as a one piece outer body over a core that can be pulled out from behind allowing the retraction mechanism to be easily pushed into place from behind, steered by the narrow nose portion. Neither does the prior art in such a combination realize the desirable non-cumulation of forces resisting retraction in order to minimize the thumb force required, having a most simple tamperproof feature and the fewest number of easily made parts. These features and more are found in the inventive combination herein further disclosed which is especially suited for high speed production and assembly at low cost.

SUMMARY OF THE INVENTION

The invention is a reliable retractable tamperproof syringe having multiple tamperproof features which operates on a principle which permits low cost parts which are few in number and well suited for high speed mass production and assembly. The syringe structure features a one piece hollow outer body having a longitudinally extending wall which is stepped. The wall comprises an elongated barrel and nose with a transition zone connecting the barrel and nose. The nose has a reduced diameter relative to the barrel. The outer body has an inwardly facing surface in the wall at the most constricted part of the transition zone where the nose begins. A plunger assembly is disposed partially within the elongated barrel with an end cap for depression of the plunger extending from an opening in the back of the barrel. The head of the plunger, which has a retraction cavity for receiving parts of a retraction mechanism, moves in slidable sealed contact with the interior of the barrel.

A retraction mechanism is lodged in the nose of the body. The retraction mechanism comprises an elongated needle holder and spring combination wherein the needle holder has an elongated body with a needle holding portion in front and a head in back. The head of the needle holder has a cooperating outwardly facing surface configured to cooperate with said inwardly facing surface along an interface oriented in the direction of retraction to produce a holding force on the needle holder when installed in the nose in the unretracted position. The needle holder and spring are easily installable from the rear of the barrel toward the nose and releaseably held by sliding engagement of said cooperating inwardly and outwardly facing surfaces while compressing the spring and thereby producing a holding force on the needle holder in opposition to the retraction force applied to the needle holder by the spring. The parts are circular in cross section.

The outwardly facing surface on the circular head of the needle holder is slightly greater in diameter than the circular inward facing surface in the wall at the most constricted portion where the nose begins. The needle holder is thus clamped in position by hoop stresses induced in the outer body and held in position by frictional holding force. The needle holder is released in response to depression of the plunger to a retraction position. Retraction occurs in response to thumb force on the plunger when a portion of the plunger passing into the transition zone separates at least a portion of the inwardly and outwardly facing cooperating surfaces thereby reducing the holding force on the needle holder to an amount less than a retraction force on the needle holder produced by the spring whereby the needle holder is retracted into the cavity a distance sufficient to withdraw an injection needle, attached to the needle holder, into the outer body.

In one embodiment, the head of the needle holder is a two part head comprising an inner head surrounded by a separable retainer member wherein the outer surface of the retainer member is the outwardly facing surface with cooperates with the inwardly facing surface in the wall to retain the needle holder in an unretracted position at the most constricted part of the transition zone where the nose begins. The retainer member is a ring member coupled to the inner head along a sliding interface oriented in the direction of retraction with a friction force which exceeds the retraction force provided by the spring. The front of the needle holder is grounded in the nose portion against forward movement. The plunger head is configured to pass through the most constricted area and push against the retainer member without also pushing against the head of the needle holder. An alternate construction of the two part head of the needle holder comprises the separable retainer member being tack welded to the inner head of the needle holder, preferably along a very small ridge or bridge between the mating surfaces which holds the two part head together until the bridge is ruptured by movement of the plunger after an injection has occurred.

The front of the plunger has an opening for a stopper slidingly fitted therein in an interference fit. The stopper is fitted in the opening in an interference fit along a sliding interface oriented in the direction of retraction. The stopper is mostly or fully dislodged by contact with the retraction mechanism at the end of an injection cycle by continued depression of the plunger from a first position at the end of the injection cycle to a second position with the tip of the plunger in contact with the retainer ring. This avoids cumulation of the force on the plunger required to dislodge the stopper from the opening and the force required to dislodge the retainer member from the head of the needle holder and outer body wall. Upon further depression of the plunger from the second position to the retraction position, the frictional holding force on the needle holder is reduced until the retraction force provided by the spring exceeds the remaining holding force and the needle holder and needle connected thereto are ejected into the cavity carrying the dislodged stopper along with them. The dislodging of the stopper and the retainer member alone make the syringe non-reusable. The plunger cannot be removed after retraction because the graspable end cap enters an opening at the back of the barrel when the plunger is depressed to the retraction position to prevent tampering after retraction.

The syringe has a high blowout pressure and a low plunger thumb force required to cause retraction. Blowout pressure is the fluid pressure operating on the stopper and retainer ring during an actual injection. High blowout pressure resistance is obtained because the retainer ring is mounted in the most constricted potion of the barrel where the nose begins which significantly reduces the amount of area exposed to fluid pressure. The smaller retainer ring allows the use of a small needle holder such that the opening in the plunger and the stopper can be only a fraction of the cross sectional area of the fluid chamber below the plunger head. The ratio of the greatest cross sectional area of the variable chamber and that of the dislodgeable stopper or the ring member are selected so that the maximum expected thumb force on the plunger during an injection will produce a maximum pressure in the chamber which will generate a blowout force on the stopper and retainer member slightly less than the amount of dislodging force necessary to dislodge the stopper and retainer member during retraction. This ratio should be at least two to one, or more preferably three to one or more, in order to ensure against premature blowout of the stopper or retainer ring.

In an alternate embodiment, the fewest number of easily made separate parts are used in a retractable syringe. The alternate embodiment has a similar stopper in the head of the plunger and a similar needle holder and spring combination with mating cooperating inwardly facing and outwardly facing interengaged surfaces at the most constricted part of a transition zone where the nose begins. In the alternate embodiment, there is no retainer ring around the head of the needle holder. Instead a tiny ramp is provided at the transition zone or adjacent the transition zone whereby the head of the plunger gently spreads the barrel outwardly while dislodging the stopper thereby reducing the damping or friction force on the head of the needle holder provided by the wall of the outer body. The holding force is thereby reduced below the retraction force provided by the compressed spring and the needle holder is ejected into the cavity of the plunger carrying the dislodged stopper along with it.

Manufacture and assembly is facilitated by the fact that the plunger and the outer body can be molded with a non-collapsible core tool that can be pulled out from behind. The parts are simply shaped and do not have hooks and parts with reentrant angles that require collapsible core pin technology. The outer body can be made in one piece and assembled from the rear. The narrowed nose portion provides no lateral space with will permit bunching of the spring and jamming when the retraction assembly is moved forward in the outer body. In fact, the nose serves as a guide to steer the parts into the proper position in one smooth stroke.

The needle does not have to be installed before the retraction mechanism is put in place because it is readily installed from the front after the needle holder is slidingly lodged in the nose. Significant variations in the holding force on the needle holder and the dislodging force on the stopper due to slight variances in the tolerance of the mating parts is avoided because the longitudinal wall of the outer body has some flexibility. The wall can spread outwardly slightly and the stopper and head of the needle holder can compress slightly radially and expand slightly in the longitudinal direction to avoid significant changes in the holding force caused by small changes in the actual diameters. Consistency in the amount of retraction force is thereby provided and economy is assured.

BRIEF DESCRIPTION OF THE DRAWINGS

FIG. 5 is a cross section along the central axis of a simplified alternate syringe structure without a retainer member around the needle holder, which is released by separation of the friction surfaces, shown in the plunger position which represents the end of an injection cycle;

FIG. 6 is the syringe structure of FIG. 5 wherein the plunger is further depressed to dislodge the stopper and begin to release the friction surfaces just prior to retraction;

DETAILED DESCRIPTION OF THE PREFERRED EMBODIMENT

Figures 1, 2:
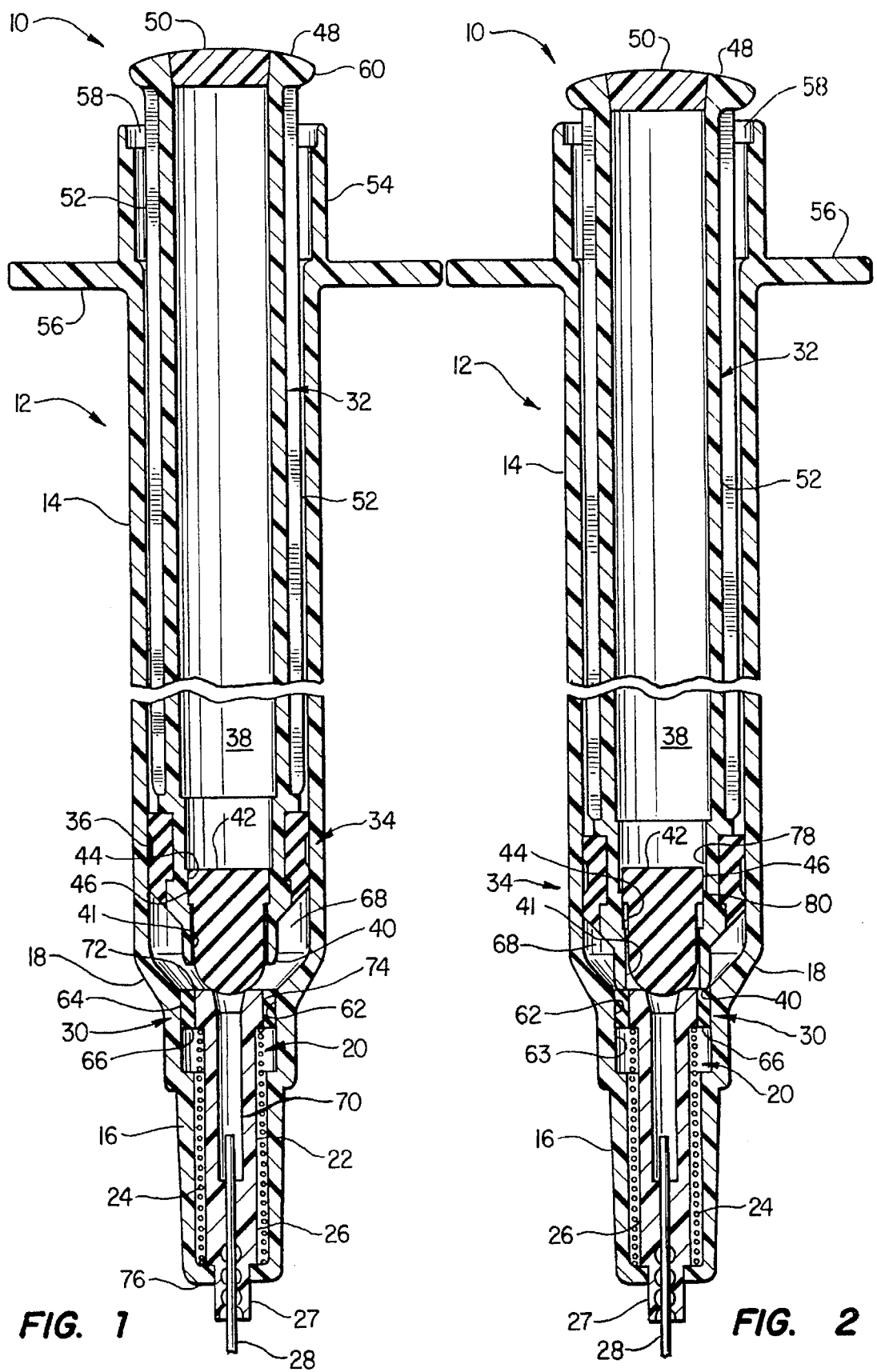
FIG. 1 is a cross section along the central axis of a first embodiment of the invention with the plunger positioned in a first position at the end of an injection cycle.
FIG. 2 is the syringe of FIG. 1 with the plunger depressed additionally to dislodge the stopper at a second position of the plunger wherein the tip of the plunger is ready to operate the retraction mechanism.

In the description that follows, like parts will be referred to by the same reference numerals. Parts with a sub script letter are mean to illustrate a minor variation of a part with the same number. The drawings are enlarged significantly in order to show the details of the invention but generally reflect the true scale which is contemplated. The parts as shown are understood to be preferably circular and symmetrical as is conventional for syringes. The drawings reflect a syringe structure having a 1 cc to 3 cc injection fluid capacity.

FIG. 1 shows the structure of the first embodiment generally referred to by reference numeral 10. Syringe 10 has a one piece hollow outer body 12. Body 12 has a longitudinally extending wall comprising an elongated barrel 14 and a nose 16 with a transition zone 18 connecting the barrel and nose. A front mounted retraction mechanism lodged in the nose is generally referred to by the reference numeral 20. It comprises the combination of an elongated needle holder 22 and spring 24. The needle holder has an elongated body with a needle holding portion 26 in front for holding a needle 28 and a head 30 in back. Head 30 may consist of a two part head as in FIGS. 1–3 or a one part head as in FIGS. 5–7. The needle holder is released by depression of a plunger that will be described.

A plunger generally designated by the reference numeral 32 is disposed for use partially within barrel 14. The plunger has a head and seal generally referred to by reference numeral 34, in slidable sealed contact with the interior of barrel 14 of outer body 12. The plunger has a seal element 36 that is conventional and a retraction cavity 38 therein.

Head 34 has a tip portion 40 forming an opening 41 into retraction cavity 38. A resilient dislodgable stopper 42 is sealingly positioned in opening 41 with a front portion thereof extending beyond tip 40. Head portion 34 and the back part of stopper 42 have cooperating lands 44, 46, respectively, which seal opening 41. Plunger 32 has an end cap 48 for depression of the plunger by the thumb. End cap 48 has a central opening for permanently receiving force fit plug 50 to close retraction cavity 38 at the back end.

Figure 4A:
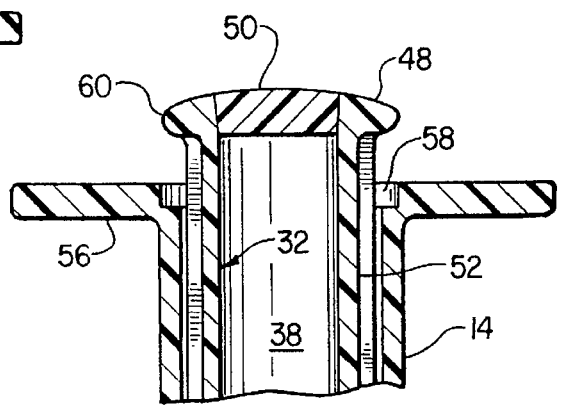
FIG. 4A is a partial cross section on the central axis of an alternate tamperproof opening in the back of the outer body prior to retraction.
Figure 4B:
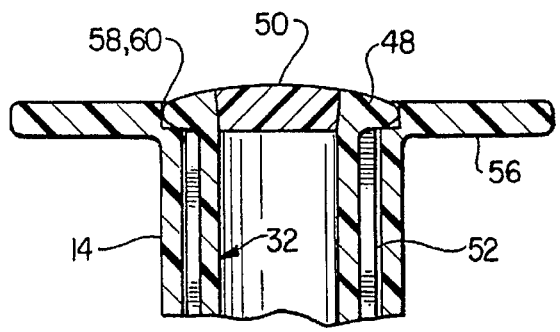
FIG. 4B is the structure of FIG. 4A with the plunger in the retracted position received in an opening at the back of the outer body.

A plurality of longitudinally extending flutes 52 slidingly support plunger 32 in barrel 14. In the embodiment of FIG. 1, outer body 12 has a collar 54 extending behind finger grips 56 having opening 58 which closely receives the outer periphery 60 of cap 48 when the plunger is depressed to the retracted position. An alternate arrangement is shown in FIGS. 4A and 4B in which barrel 14 is extended longitudinally, if necessary, so that end cap 48 fits closely within an opening at the back of the barrel where the finger grips are. FIG. 4B shows the tamperproof position with the plunger in the retracted position. It should be noted that depending on the relationship of the inside diameter of the barrel and the diameter of the end cap, the end cap could instead be received right inside the opening at the back of the barrel. Regardless of how the end cap in back of the outer body and barrel are configured, the plunger can no longer be grasped after retraction has occurred because end cap 48 is depressed into an opening.

The wall of outer body 12 and head 30 of the needle holder have mating cooperating smooth surfaces which hold needle holder 22 in the position shown in FIG. 1 with spring 24 compressed. Nose 16 has a reduced diameter relative to the barrel. The outer body has a most constricted part where head 30 of needle holder 22 is engaged and held. The outer body has an inwardly facing surface 62 at the most constricted part of the transition zone where nose 16 begins. Similarly, head 30 has an outwardly facing surface 64 configured to cooperate with inwardly facing surface 62 to produce a holding force on needle holder 22 when the retraction mechanism is installed in the nose from the rear. Mating surfaces 62, 64 constitute a sliding interface oriented in the direction of retraction, which seals nose 16. Mating surfaces 62, 64 are preferably friction surfaces which have an interference sliding fit to apply a frictional holding force which holds needle holder 22 in position by friction between the mating parts. It is within contemplation of the invention that one or more of the cooperating interface surfaces could employ a coating or adhesive bond which is ruptured or released when the mating surfaces or lands are separated or moved relative to each other.

Head 30 provides a lower boundary for a variable fluid chamber 68 below head 34. Needle holder 22 has a fluid path 70 in fluid communication with fluid chamber 68 and needle 28. Needle holder 22 has a smaller diameter inner head 72 which is part of head 30. Retainer member 66 is coupled to inner head 72 along sliding interface 74 oriented in the direction of retraction. Retainer member 66 is coupled to inner head 72 with a holding force which exceeds a retraction force applied to the underside of inner head 72 by means of the end of compressed spring 24. A reduced diameter portion 27 of needle holder 22 protrudes through an opening in front 76 of nose 16.

Importantly, retainer member 66 can be visualized as an annular ring surrounding circular inner head 72. The location of retainer member 66 at the most constricted part of the transition zone where the nose begins and the relatively small area exposed to pressurized fluid in chamber 68 results in a high blowout pressure. Since the front portion 26 of the needle holder is grounded or bottomed inside front 76 of nose 16, no amount of pressure will allow needle holder 22 or needle 28 to move forward. Blowout pressure may be defined as the pressure in chamber 68 acting on the exposed area of retainer member 66 to produce a force sufficient to overcome the holding force such that retainer 66 could "blowout" by moving forward and prematurely release needle holder 22.

Some users have strong hands and might, at the outer limit in an emergency, be able to generate a force of as much as fifteen to eighteen pounds on the plunger during an injection. It is considered almost impossible for anyone to exert a force of more than eighteen pounds. This may be regarded as the maximum expected force which must be taken into account so that ring member 66 will not blowout while an injection is being made. The greatest cross sectional area of variable chamber 68 and the area of retainer member 66 exposed to fluid pressure are selected so that the blowout pressure is higher than the maximum pressure in chamber 68 expected to result from the maximum expected thumb force applied to cap 48 during an injection. This milo is preferably about two to one and more preferably about three to one or more so that the holding force holding the retraction mechanism in place can be kept at a comfortably low level while the blowout pressure remains high.

Dislodgeable stopper 42 has a similar blowout problem to recognize. The front and middle portion of stopper 42 are relieved slightly from opening 41 such that the fluid pressure in chamber 68 is directed against the cross sectional area at cooperating lands 44, 46 and could cause stopper 42 to blowout. A frictional holding force is generated at the lands 44, 46 which may be called a dislodging force which must be overcome to slide stopper 42 rearwardly before retraction. The ratio of the maximum cross sectional area across the interior of variable chamber 68 to the maximum cross sectional area of stopper 42 exposed to pressure in chamber 68 are selected so that the maximum expected thumb force on plunger 32 during an injection will produce a maximum force slightly less than the amount of dislodging force necessary to dislodge the stopper so that stopper 42 will not blowout during an injection. This ratio is preferably not less than about two to one, more preferably three to one or more, whereby a force of about eighteen pounds on the plunger, for example, would produce a pressure generated force of only about nine or six pounds, respectively, on the stopper, so that the stopper can be easily dislodged in advance of retraction at the end of the injection cycle but will not blowout during an injection. The stopper is dislodged after the injection by thumb force applied to the stopper by movement of the plunger.

The components used for retraction are arranged to avoid cumulation of force during the retraction sequence. In FIG. 1, stopper 42 has a forward extension beyond tip 40 which allows full thumb pressure to be applied to the stopper before any other portion of the retraction mechanism is engaged. The amount of forward extension beyond tip 40 is related to the length of lands 44, 46 such that the forward extension of stopper 42 preferably represents about 80 percent of the engaged land length. When stopper 42 is moved back until the front is even with tip 40, as seen in FIG. 2, only about 20 percent of engaged land remains. In FIG. 2 it can be seen that thumb force on plunger cap 48 has been applied to partially dislodge stopper 42 such that a gap 78 is created and the remaining engaged land area is represented as area 80.

Since I believe the amount of frictional holding force or dislodging force is roughly proportional to the amount of the length of the sliding interface between cooperating lands 44, 46, it follows, ignoring dynamic effects, that the amount of force remaining decreases as the engaged sliding interface area is reduced. This is what happens as stopper 42 moves back into cavity 38 from the position of FIG. 1 to the position of FIG. 2. It is believed appropriate to set the initial dislodging force to allow about five pounds at the position of FIG. 1 which is reduced to about one pound remaining when the stopper or plug member 42 reaches the position of FIG. 2. It might be noted at this point in the description that the front portion of tip 40 preferably has some longitudinally extending slits or openings so that fluid is not trapped in the trapezoidal shaped area of chamber 68, seen in FIG. 2, because of contact between tip 40 and the upper surface of retainer ring 66.

Needle holder 22 and spring 24 are combinably installable from the rear of the barrel before the plunger is assembled and releasably held at the most constricted part of the transition zone where the nose begins by sliding engagement of the cooperating inwardly and outwardly facing friction surfaces 62, 64 while compressing spring 24. The length of the engaging land 64 and the amount of interference fit is preferably designed to provide a frictional holding force in opposition to the retraction force provided by the compressed spring 24 of somewhere around five pounds even though the spring may apply a retraction force in the retraction direction of somewhere around a half pound. In use the needle is pushed against a rubber seal in a vial so the needle holder must resist a resulting backward force without being dislodged during the filling operation. This requirement and blowout pressure limits the low end of the holding force on the needle holder.

Figure 3:
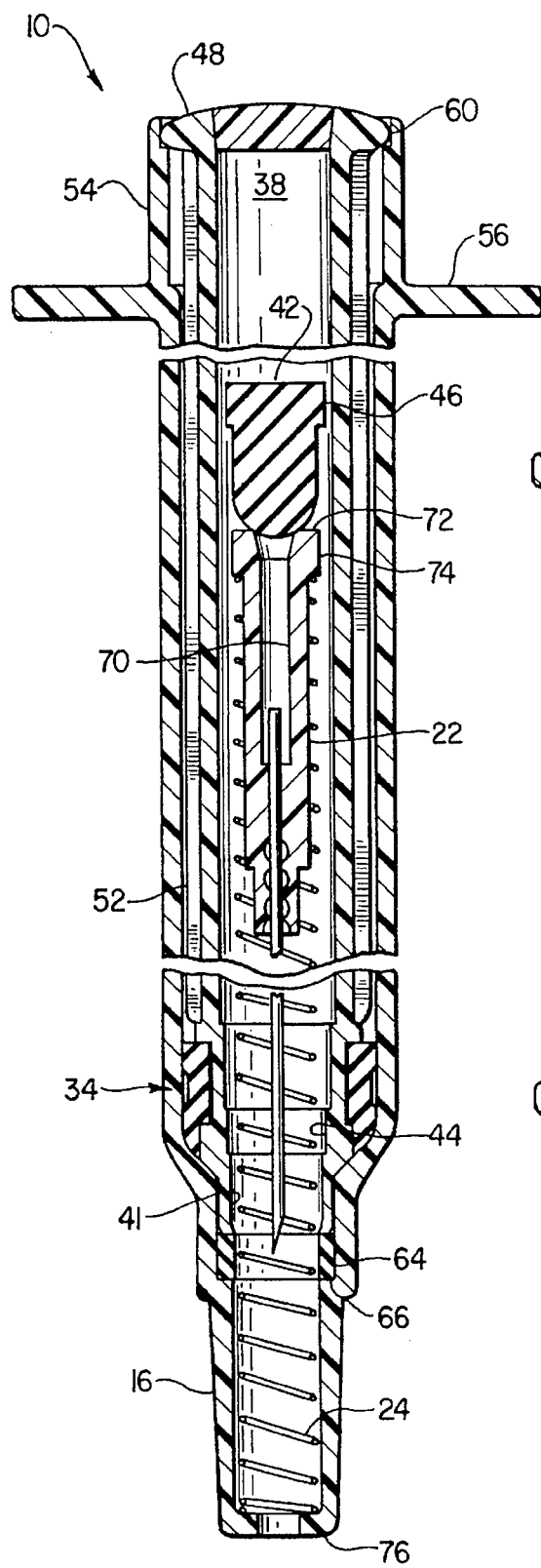
FIG. 3 is the syringe of FIG. 2 wherein the plunger has been further depressed to a retraction position, retraction has occurred and the cap at the back of the plunger is closely received in an opening at the back of the outer body.

Referring again to FIG. 2, it can be seen that further depression of the plunger beyond the second position of FIG. 2 dislodges retainer ring member 66 along the sliding interface 74 provided by the outer surface of inner head 72 and along the inwardly facing friction surface 62. As the amount of remaining engaged interface is reduced, the amount of force required to continue moving retainer member 66 off needle holder 22 is reduced and the small remaining engagement area 80 between lands 44, 46 of the plunger and stopper preferably cause stopper 42 to be dislodged before needle holder 22 is released. When the remaining residual friction force during continued depression of the plunger becomes less than the retraction force provided by compressed spring 24, the retraction position of FIG. 3 is reached whereby retraction occurs.

When retraction occurs needle holder 22 moves through opening 41 into cavity 38. The uncompressed length of spring 24 is selected to provide backward movement sufficient to withdraw an injection needle 28 fixed in front portion 26 entirely within outer body 12, carrying dislodged stopper 42 with it. At the same time, cap 48 enters opening 58 of the barrel with peripheral edge 60 closely confined, in order to prevent tampering after retraction. It is immaterial whether cap 48 moves into the opening at the instant of retraction or after retraction has already occurred because the movement is automatic due to the continued thumb force applied to trigger the retraction. Sufficient unengaged length of inwardly facing friction surface 62 is provided so that retainer member 66 can move downwardly a sufficient distance to reach the retraction position of FIG. 3. After retraction, retainer member 66 preferably remains stuck and prevents any possibility of any one being able to reengage it with the head of needle holder 22. The diameter of land 62 in the area designated 63 can be increased slightly to provide relief for retainer ring 66 as it is pushed down by tip 40.

Figure 8:
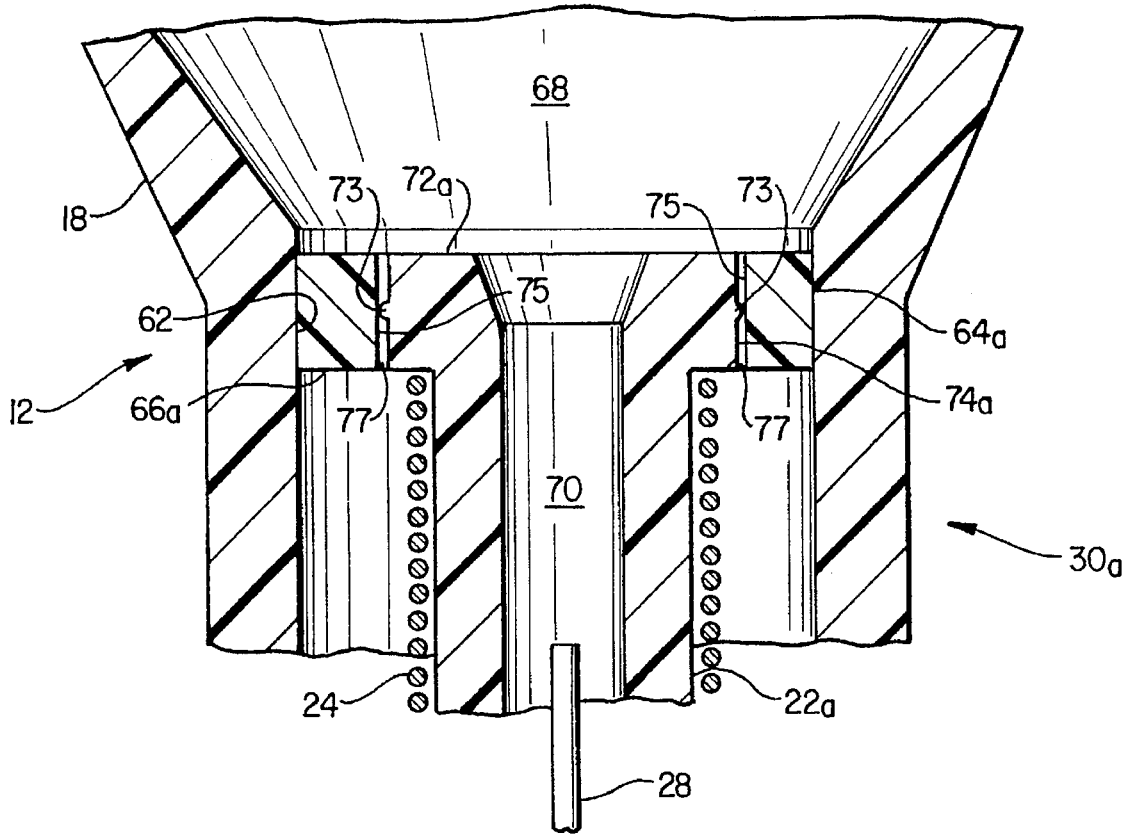
FIG. 8 is a schematic longitudinal cutaway view in elevation through the center of the two part head showing how a tack weld can be applied to simultaneously seal and hold the retainer ring in place on the needle holder.

It is also within the contemplation of the invention that separable retainer member 66 may be removably coupled to inner head 72 of needle holder 22 by means of a relatively small in area "tack" weld which is sufficient to resist the retraction force applied to needle holder by spring 24 but which can be ruptured or separated by depression of the plunger beyond the position shown in FIG. 2, to release the needle holder and allow retraction. This is schematically illustrated in FIG. 8 with respect to alternate head 30a with the parts of syringe body 12 and needle holder 22 cutaway to focus on the modification. The remainder of the syringe structure would be like FIGS. 1–3.

In FIG. 8, inner head 72a has an outwardly facing surface 74a and a very small raised portion or series of horizontally spaced apart raised potions 73 around the periphery in a continuous band or annular ring which extend relatively uniformly outwardly beyond peripheral surface 74a of head 72a. The raised portion could be on the inner surface 75 of retainer 66a instead of being on surface 74a of the needle holder. The head of the needle holder is preferably circular but could be conceivably another shape with the retainer member 66a correspondingly configured to conform to it.

The inwardly facing surface 75 of inner head 72a is in contact with raised portion 73 on the outer surface of inner head 72a and there may be a small gap 77 between them all around. The raised potion 73 couples retainer 66a to inner head 72a and may be referred to as a bridging portion which resists the blowout pressure referred to above and holds the needle holder in place against the retraction force imposed on the needle holder by spring 24 together with any small additional forces that may be applied when the needle is pushed against the rubber seal of a vial in preparation for use. The bridging portion may be formed by "tack" welding the raised portion 73 to the inner surface of the ring 66a or by providing any other form of frangible bridging portion that holds the separable ring member 66 and needle holder head 72a together. It is required that however done, the bridging portion must also serve as a seal between the facing surfaces of the ring member and inner head so that fluid under pressure cannot pass from chamber 68 through gap 77 to reach the nose portion of the device. All fluid must pass through fluid passage 70.

It can be seen that when the position of FIG. 2 is reached the front tip 40 of the plunger presses against retainer ring 66a after stopper 42 is almost dislodged and uncouples the retainer ring 66a from the inner head 72a of needle holder 22a. Any tack weld connecting the separable parts at the bridging portion is ruptured, fractured or otherwise separated so as to separate retainer ring 66 a from inner head 72a thus releasing needle holder 22a from further restraint. They and the force applied by spring 24 causes retraction to occur much as before described and shown in FIG. 3.

It is believed that the increased diameter of the raised portion 73 should be within the range of about 1 to 8 thousandths of an inch which may be dictated by the ability of the molding equipment available to produce a consistent bridging portion without defects. It is believed that it may be desirable to employ different polymeric materials for the retainer ring and needle holder to facilitate tack welding, such as a suitable polyvinyl chloride (PVC) for the retainer ring and a suitable polycarbonate plastic material for the needle holder. One way to couple these two parts may be to assemble them and expose them to a temperature of about 120° C. for twenty minutes or so to allow some diffusion or incipient melting to occur where they touch. The raised potion creates a high unit pressure where it comes into contact with the inwardly facing surface of retainer 66a. Sonic welding could also be employed. A coating or adhesive which couples the retainer ring to the needle holder and can be uncoupled by means of force applied to the retainer ring by the plunger is also within the contemplation of the invention.

Figure 7:
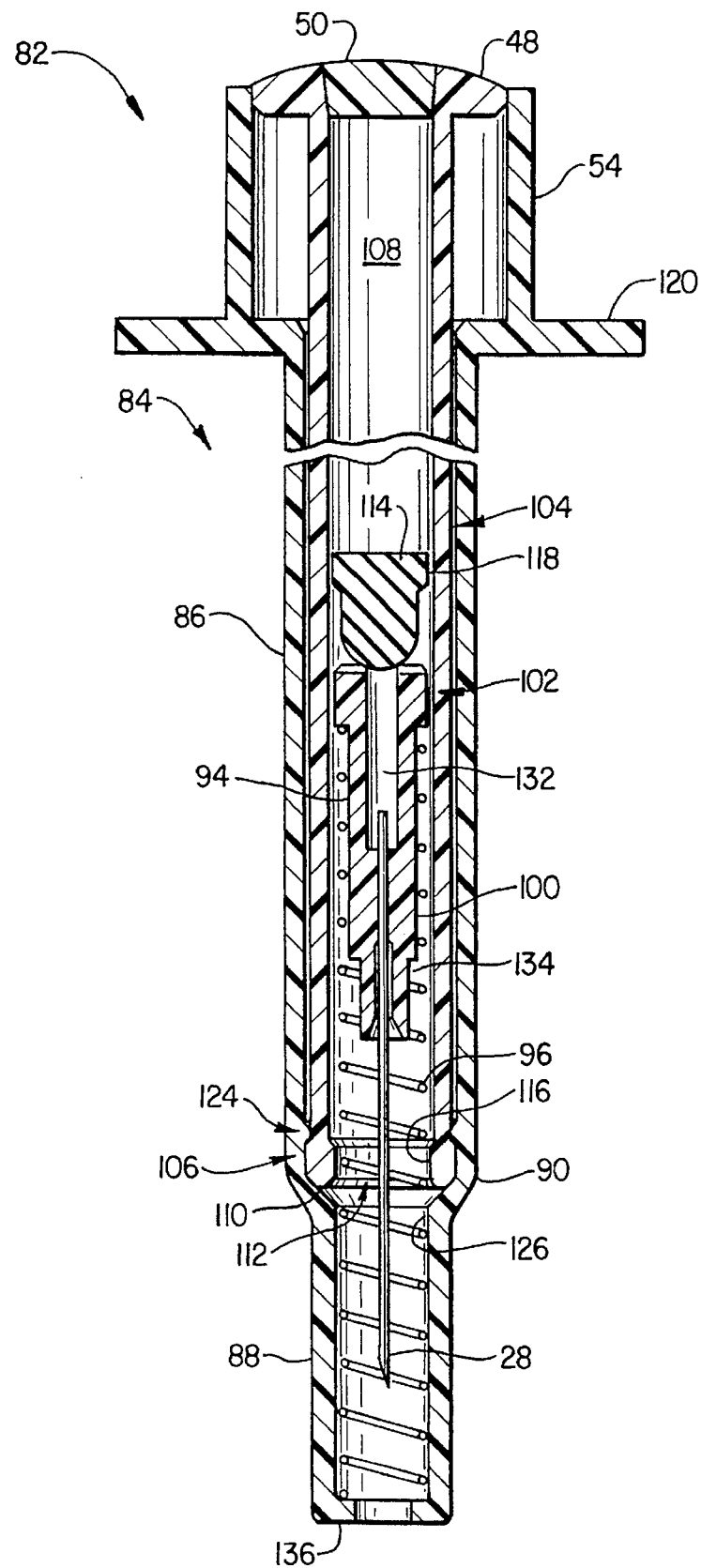
FIG. 7 is the syringe structure of FIG. 6 with the plunger further depressed beyond the position of FIG. 6 to the retraction position where retraction has occurred and the cap is secure within an opening in the back of the hollow outer body.

An alternate syringe 82 is disclosed in FIGS. 5–7. In FIG. 5, Syringe 82 has a one piece hollow outer syringe body 84. Body 84 has a longitudinally extending wall comprising an elongated barrel 86 and a nose 88 with a transition zone 90 connecting the barrel and nose. A front mounted retraction mechanism lodged in nose 88 is generally referred to by the reference numeral 92. It comprises the combination of an elongated needle holder 94 and spring 96. The needle holder has an elongated stem body with a needle holding portion 100 in front for holding needle 28 and a head 102 in back. In this ease, head 102 is a one part head integral with the rest of needle holder 94. Spring 96 delivers a retraction force in a retraction direction to the underside of head 102.

A plunger generally designated by reference numeral 104 is disposed for use partially within barrel 86. Plunger 104 has a head portion 106 which moves in slidable sealed contact with the interior of barrel 86 of outer body 84. Although a separate seal might be used on head 106, this embodiment is suitable for a smaller diameter, such as a Ice syringe, and can be used with head 106 also serving as the seal. A retraction cavity 108 is provided in the interior of hollow plunger 104. Head 106 has a tip portion 110 forming an opening 112 for a dislodgable stopper 114 having a front portion extending beyond tip 110. Head portion 106 has an inwardly facing land 116 and the back of stopper 114 has an outwardly facing land 118 comprising cooperating friction surfaces which seal opening 112. The back portion of outer body 84 may have finger grips 120 and the same collar 54 and end cap 48 previously disclosed. The alternate arrangement of FIGS. 4A and 4B may also be employed.

The outer portion of tip 110 may be equipped with an angled surface 122 designed to cooperate with a small ramp surface 124 located in the vicinity of transition zone 90. The wall of outer body 84 and head 102 of the needle holder have mating cooperating friction surfaces which frictionally hold needle holder 102 in the position shown in FIG. 5 with spring 96 compressed. Nose 88 has a reduced diameter relative to barrel 86. The outer body has a most constricted part where the head 102 of needle holder 94 is frictionally engaged. The outer body has an inwardly facing surface or land 126 at the most constricted part of the transition zone where nose 88 begins. Similarly, head 102 has an outwardly facing friction surface 128 configured to cooperate with inwardly facing surface 126 to produce a frictional holding force on needle holder 94 when the retraction mechanism is installed in the nose from the rear.

Mating surfaces 126, 128 constitute a sliding interface oriented in the direction of retraction, which seal nose 88. Mating surfaces 126, 128 are preferably smooth friction surfaces which have an interference sliding fit when needle holder 94 is installed from the rear whereby a frictional holding force holds needle holder 94 in position by friction between land 126 and head 102 of needle holder 94. It is within contemplation of the invention that one or both of these surfaces could have a coating or adhesive bond which is ruptured when the mating surfaces are separated to release the needle holder.

Head 106 provides the upper boundary for a variable fluid chamber 130 below head 106. Needle holder 94 has a fluid path 132 in fluid communication with chamber 130 and needle 28. Needle holder 94 is releasably coupled at surfaces or lands 126, 128 with a holding force that exceed the retraction force applied to the underside of head 102 by the end of compressed spring 96. A reduced diameter portion 134 of needle holder 94 protrudes through an opening in front 136 of nose 88. Blowout pressure is not a factor with respect to the needle holder on the alternate embodiment. No amount of pressure will allow needle holder 94 or needle 28 to move forward since the front portion 100 of the needle holder is grounded or bottomed inside front 136 of nose 88.

Blowout pressure is still a factor to be considered in connection with stopper 114. Blowout pressure would be the pressure in chamber 130 produced by thumb force on cap 48 acting on the cross sectional area of stopper 114 which could overcome the holding force, causing stopper 114 to dislodge from opening 112 prematurely. The ratio of the maximum cross sectional area across the interior of variable chamber 130 to the maximum cross sectional area of stopper 142 exposed to pressure in chamber 130, and the dislodging force necessary to dislodge stopper 144, are selected so that the maximum expected thumb force on plunger 104 during an injection will not cause the stopper to blowout. Yet the stopper will still be dislodged by the dislodging force on the plunger once the front of stopper 114 contacts the retraction mechanism after the injection has ended. The ratio referred to is preferably not less than about two to one, or more preferably about three to one or more, whereby a force of about eighteen pounds on the plunger, for example, would produce a pressure generated force of only about nine or six pounds respectively, on the stopper, so that the stopper can be easily dislodged in advance of retraction at the end of the injection cycle but will not blowout during an injection. The smaller diameter stopper allows two or three times the thumb force to be used during the injection cycle than required to actually dislodge the stopper by direct application of force.

By reference to FIGS. 5-7, the operation and further features of the alternate embodiment are discussed. The syringe is used in the normal manner until the plunger is depressed to the first position of FIG. 5 which is the end of the injection cycle. Stopper 114 has a forwardly extending end which has come into contact with head 102 of needle holder 94 to block fluid path 132. Further depression of plunger 104 toward the position of FIG. 6 mostly or fully dislodges stopper 114 and begins spreading barrel 84 at the transition zone by sliding contact between head potion 106 and ramp 124. Ramp 124 is a very small inwardly extending annular thickening of the wall of barrel 86 which can take many shapes or forms. For example, ramp 124 may be a small step 125 in the wall which continues vertically downward as indicated by the dotted fine, which is somewhat exaggerated in FIG. 5.

The barrel is flexible and is spread outwardly a slight amount to the position of FIG. 6 just prior to retraction. Here the mating surfaces 126, 128 are separated an amount which reduces the clamping force on the needle holder 94. The spreading shown in FIG. 6 is greatly exaggerated for illustration. It is estimated that an expansion of only about four thousandths of an inch is sufficient to release needle holder 94 from nose 88. By slight further depression of the plunger from the position of FIG. 6 to the retracted position of FIG. 7, retraction occurs when the retraction force applied by spring 96 exceeds the remaining holding force on needle holder 94. Needle holder 94 then moves through opening 112 into cavity 108 along with a portion of spring 96. The uncompressed length of spring 96 is designed to provide sufficient backward movement to withdraw an injection needle 28 fixed in front portion 94 and carry dislodged stopper 114 with it. At the same time, cap 42 enters opening 138 at the rear of a barrel extension 54 where the peripheral edge is closely confined in order to prevent tampering after retraction.

The location and configuration of ramp 124 is arranged to avoid cumulation of force required during the retraction sequence. Most of stopper 114 should be dislodged by thumb pressure on plunger 104 before significant resistance develops as angled surfaces 122 begin pushing outwardly on ramp 124. The selection of the location of ramp 24 and the angle of the engaging surfaces make it possible to have a fairly smooth continuous force since the dislodging force continuously decreases as the sliding interface area 116, 118 between the plunger and the stopper is linearly decreased. Because ramp 124 is relatively very small, it is still possible to remove a stepped molding core from the rear of the outer body 84. Alternately, ramp 124 can be the smaller diameter step 125 which avoids reentrant angles whereby resistance to removal of the molding core could occur. After retraction, the back of the plunger is unaccessible and there is no way to reach to stopper or the needle holder in order to reinstall them for re-use.

In operation, there are many advantages to the improved combination disclosed herein. The diameter of the stopper in both embodiments and the slidable retaining ring member in the first embodiment, in relation to the diameter across the fluid chamber, makes it possible to produce a syringe which withstands high blowout pressure. By minimizing the effective surface area exposed to the pressurized fluid during an injection, the syringe will withstand injection thumb force of around fifteen to eighteen pounds during injection and at the same time retract in response to as little as five to six pounds of force on the plunger once the injection fluid has been injected. Once the fluid has been injected, cumulation of force required to concurrently operate the retraction mechanism is avoided. First the stopper is moved back and then the needle holder is released. By constricting the diameter of the syringe near a transition zone where the nose begins, a constriction enables the needle holder to be smaller which in turn allows it to fit in a smaller opening with a smaller stopper in the retraction cavity of the hollow plunger.

A vacuum must be pulled in order to fill the syringe. The ring member or the needle holder, as the case may be, must seal the front nose of the syringe body because otherwise vacuum could be lost and fluid could enter the spring area and leak out the front. The hollow outer body and syringe plunger are preferably made from conventional plastic material used for syringes, which has some flexibility. The tolerances on the diameter of mating facing surfaces between the head of the needle holder and the barrel and between the stopper and head of the plunger are not critical in order to maintain a consistent holding and dislodging force. This is believed to be because increasing interference fit increases the frictional holding force only up to a point and then the surrounding wall simply expands a small amount or the internal parts are compressed a small amount without a corresponding increase in the longitudinal force required to move the retainer member or plug member in the retraction direction. It is a desirable self correcting mechanism which is a cost and quality benefit in making the parts. It is believed that a plastic retainer member could be used and the same self limiting fictional holding force would be obtained.

In the best mode the stopper and the ring member are preferably made from a thermoplastic rubber material designated number 181-55 available from Advanced Elastomer Systems, 540 Maryville Centra Drive, St. Louis, Mo. and sold under the trade name Santoprene®. It is said to have a characteristic hardness around 55 on the Shore A durometer scale which allows for the right amount of resistance to compression, fluid resistance such that the material does not swell when in contact with most fluids, environmental stability allowing the friction and sealing properties to remain non-temperature sensitive, good property retention after aging and excellent property retention after sterilization by all accepted methods. The plunger seal around the head of the plunger is conventional.

The parts are few in number and easily mass produced. The alternate embodiment has the fewest number of separate parts of any tamperproof retractable syringe. The plunger has a one piece hollow outer body with a transition zone and a narrow nose portion. The internal diameter is stepped to greater diameters from front to back for molding around a non-collapsible core which can be extracted from the rear. The same is true for the plunger.

Assembly is greatly simplified and can be accomplished with high speed mechanized equipment. The needle holder and spring are installable from the rear of the barrel without the needle. In the first embodiment the retainer member is forced fit over the inner head of the needle holder and the assembly together with the uncompressed spring are pushed forward and held by sliding engagement of the cooperating inwardly and outwardly facing surfaces while compressing the spring. The front of the needle holder passes through an opening in the nose which makes it easy to install the needle from the front by conventional means. The alternate embodiment is installed the same way except that there is no separable retainer member around the head of the needle holder.

The narrow nose provides a particular advantage for mechanized assembly. The nose has a wall defining an elongated internal cavity which closely confines the spring and needle holder combination. During installation this cavity serves as a guide to steer the needle holder and uncompressed spring into a compressed state of the spring. This solves an important assembly problem. If there is much lateral space in the nose around the spring, when the uncompressed spring is being compressed, it is a laterally unstable column which flexes sideways and bunches up causing a jam up. It might be added that rounded edges on the bottom of the slot directly below retainer 66 would further facilitate entry of the end of the spring.

The stopper is also installable from the rear of the plunger by pushing it forward until the cooperating lands are slidingly engaged. Then plug member 50 is force fit or otherwise fixed in the opening at the back of the plunger and the plunger is installed in the outer body. It is not necessary to try to pass the sharp needle through an elongated body with constricted openings where slight misalignment could cause hangups. The head of the needle holder simultaneously acts as a seal as well as a holding device such that no seal is required at the tip of the nose and no ultrasonic welding of separate parts is required.

There is no necessity for using internal locking teeth of any kind. No locking teeth are needed to hold the retraction mechanism or to lock the plunger after retraction. Locking teeth present difficult molding and quality control problems, tend to be temperature sensitive and tend to require a larger diameter barrel which increases premature blowout problems. In addition to the non-reusability provided by separation of the retainer ring from the head of the needle holder and dislodgement of the stopper, the plunger is not accessible after retraction because it is depressed within an opening at the back of the outer body. This additional tamperproof feature is provided in a one piece body without the necessity for hooking anything or twisting anything. The easily made and installed force fit plug at the back of the retraction cavity prevents access to the retracted components. The Federal government has fights in the invention under 35 U.S.C. §203. The Federal government has a nonexclusive, nontransferable irrevocable, paid up license to the invention.

I claim:

1. A tamperproof retractable syringe for injecting fluid wherein the syringe has a one piece body and a retraction mechanism assembleable from the rear which resists high blowout pressure during an injection but can be retracted with low plunger force after an injection, comprising:

a one piece hollow outer body having a longitudinally extending wall, comprising an elongated barrel and nose, with a transition zone connecting the barrel and nose, the nose having a reduced cross sectional area relative to the barrel and an inwardly facing surface in the wall at the most constricted part of the transition zone where the nose begins;

a plunger assembly disposed partially within the elongated barrel, the plunger having a head in slidable sealed contact with the interior of the outer body, a forward portion and a retraction cavity therein for receiving parts of a retraction mechanism;

a retraction mechanism sealingly disposed in the nose, the retraction mechanism having a retractable part comprising a needle holder having an elongated body having a needle holding tip portion in front and a head in back, a passageway defining a fluid path into a variable fluid chamber in the barrel below the plunger, and a spring applying retraction force to the retractable part, said retractable part being configured to be able to retract into the retraction cavity of the plunger when retraction is initiated;

the retraction mechanism further including a nonretractable part comprising a retainer member surrounding the head of the needle holder, the retainer member and said head of the needle holder being removably coupled by a bridging portion between them;

the needle holder and spring being installable into the nose from the rear of the barrel and releaseably installed by sliding engagement of said retainer member and said inwardly facing surface while compressing said spring, said sliding engagement producing a holding force in opposition to the retraction force applied to the needle holder by said spring; and the plunger being depressible to a first position which comprises the end of an injection cycle whereby fluid previously drawn into the variable chamber is expelled through said fluid path, and a retraction position beyond said first position wherein retraction is initiated by the forward portion of the plunger head moving through the transition zone in the nose to release the needle holder by uncoupling the retainer member and needle holder at said bridging portion thereby reducing the holding force to an amount less than the retraction force on the needle holder to cause retraction of the retractable part into the retraction cavity of the plunger.

2. The tamperproof retractable syringe of claim 1 wherein said bridging portion constitutes a raised portion on one of the retainer member or the needle holder comprising a tack weld which is separated to uncouple the retainer member from the needle holder.

3. The tamperproof retractable syringe of claim 1 wherein the head of the needle holder and retainer member at the most constricted part of the transition zone where the nose begins comprise a lower boundary for the variable fluid chamber below the plunger head.

4. The tamperproof retractable syringe of claim 3 wherein the ratio of the greatest cross sectional area of the variable chamber to the area of the retainer member exposed to pressurized fluid in the variable chamber at the lower boundary during an injection is selected so that the retainer member has a high blow out pressure higher than the maximum expected pressure resulting from the maximum expected thumb force on the plunger so that the retainer member will not blowout prematurely during an injection.

5. The tamperproof retractable syringe of claim 4 wherein the ratio of the greatest cross sectional area of the variable chamber to the cross sectional area of the retainer member exposed to fluid in the variable chamber at the lower boundary is not less than about two to one so that high fluid pressure can be resisted while retaining a relatively low force on the plunger necessary to cause retraction.

6. The tamperproof retractable syringe of claim 5 wherein said ratio is not less than about three to one for improved resistance to high blowout pressure.

7. The tamperproof retractable syringe of claim 1 wherein the forward portion of the plunger head has an opening therein leading to the retraction cavity, said opening being sealingly closed by a dislodgeable stopper which slides relative to the plunger in response to dislodging force applied to the stopper by depression of the plunger at the end of the injection cycle before the initiation of retraction occurs.

8. The tamperproof retractable syringe of claim 7 wherein the dislodgeable stopper has an extended forward end which contacts the needle holder at the end of an injection whereby said dislodging force is applied during continued depression of the plunger prior to the initiation of retraction.

9. The tamperproof retractable syringe of claim 7 wherein the ratio of the greatest cross sectional areas of the variable chamber and the dislodgeable stopper is selected so that the maximum expected thumb force on the plunger during an injection will produce a maximum pressure in the chamber fluid which will generate a force on the stopper less than the amount of dislodging force necessary to dislodge the stopper so that the stopper will not blowout prematurely during an injection.

10. The tamperproof retractable syringe of claim 9 wherein said ratio of the cross sectional area of the variable chamber to the cross sectional area of the dislodgeable stopper is at least about two to one so that at least twice the force necessary to dislodge the stopper can be applied to the plunger during an injection without blowout of the stopper.

11. The tamperproof retractable syringe of claim 10 wherein said ratio is at least about three to one.

12. The tamperproof retractable syringe of claim 3 wherein the forward portion of the plunger head has an opening therein leading to the retraction cavity, said opening being sealingly closed by a dislodgeable stopper which slides relative to the plunger in response to dislodging force applied to the stopper by depression of the plunger at the end of the injection cycle before the initiation of retraction occurs.

13. The tamperproof retractable syringe of claim 12 wherein the ratio of the greatest cross sectional area of the variable chamber to the area of the retainer member and to the area of the stopper exposed to pressurized fluid in the variable chamber during an injection are selected so that the maximum expected thumb force on the plunger during an injection will produce a pressure force on the stopper and retainer member slightly less than the amount necessary to dislodge them so that they will not blowout during an injection.

14. The tamperproof retractable syringe of claim 13 wherein said ratios are not less than about two to one.

15. The tamperproof retractable syringe of claim 14 wherein one of said ratios is not less than about three to one.

16. The tamperproof retractable syringe of claim 1 wherein the plunger has a graspable end cap for depressing the plunger and a length selected to allow the end cap to enter an opening of the barrel when the plunger is depressed to cause retraction in order to prevent tampering.

17. A method of assembling a tamperproof retractable syringe which is well suited for automated assembly;
providing a one piece hollow syringe body having a longitudinally extending wall with an open back end, comprising an elongated barrel and nose portion of reduced cross sectional area relative to the barrel, and an inwardly facing surface in the wall at the most constricted part of a transition zone between the barrel and nose where the nose begins;

providing a needle holder having a fluid path, the needle holder having an elongated body portion in front and a head end in back, and providing a spring under the head end which circumscribes the needle holder;

providing a retainer member having an opening surrounded by a wall wherein the wall has an inner surface which defines the opening, said opening being sized to receive and releasably couple the head of the needle holder with a holding force which exceeds a retraction force applied to the needle holder by the spring, said retainer member having an outwardly facing surface sized to slidingly and frictionally engage said inwardly facing surface in the nose against said retraction force which is provided when the spring is compressed within the nose;

installing the retainer member on the head end of the needle holder;

loading the spring followed by the needle holder into the back opening in the barrel part of the syringe body and positioning at least the forward portion of the spring and a portion of the elongated body of the needle holder within the nose;

moving the head end of the needle holder and the coupled retainer member into the most constricted part of the transition zone where the nose begins; and installing the coupled needle holder and retainer member in the nose by sliding engagement of the outwardly facing surface of the retainer member with the inwardly facing surface in the wall while compressing the spring within the nose.

18. The method of claim 17 further including the step of mounting a needle in the front of the elongated body portion in communication with the fluid path after the coupled needle holder and retainer member are installed in the nose.

19. The method of claim 17 further including the steps of providing a plunger assembly having a front portion and a back portion, the front portion including a head configured for sliding sealed contact with the interior of the outer body and installing the front portion of the plunger assembly into the barrel through the open back end.

20. The method of claim 17 wherein the step of installing the coupled needle holder and retainer member in the nose include the step of grounding the needle holder in the nose to prevent forward movement of the needle holder relative to the nose after installation.

21. The method of claim 20 wherein the needle holder is provided with a tip in front of the elongated body portion and the step of grounding the needle holder in the nose includes the step of causing the tip to project forwardly beyond the nose.

22. The method of claim 21 further including the step of mounting the needle in said tip of the needle holder in communication with the fluid path.

23. The method of claim 17 wherein the nose has a wall defining an internal cavity which closely confines the spring and needle holder combination and the step of positioning at least the forward portion of the spring includes the step of using this cavity as a guide to steer the needle holder and uncompressed spring into a compressed state of the spring.

24. A method of assembling a tamperproof retractable syringe which is well suited for automated assembly;
providing a one piece hollow syringe body having a longitudinally extending wall with an open back end, comprising an elongated barrel and nose portion of reduced cross sectional area relative to the barrel, and an inwardly facing surface in the wall at the most constricted part of a transition zone between the barrel and nose where the nose begins;

providing a plunger assembly having a front portion and a back portion, the front portion including a head configured for sliding sealed contact with the interior of the elongated barrel, said head having a retraction cavity and a leading end configured to contact and remove a retainer member from a needle holder to be mounted in the nose;

providing a needle holder having an elongated body portion in front and a head in back with a fluid path therethrough, the head of the needle holder having a retainer member which can be separated from the head of the needle holder by contact with the leading end of the plunger, the retainer member having an outwardly facing surface configured to slidingly and frictionally engage said inwardly facing surface in the nose and hold the needle holder against a retraction force provided by the spring when the spring is compressed within the nose;

loading the spring followed by the needle holder into the back opening in the barrel part of the syringe body and positioning at least the forward portion of the spring and a portion of the elongated body of the needle holder within the nose;

moving the head end of the needle holder and the retainer member into the most constricted part of the transition zone where the nose begins; and installing the needle holder and retainer member in the nose by sliding engagement of the outwardly facing surface of the retainer member with the inwardly facing surface in the wall while compressing the spring within the nose.

25. The method of claim 24 further including the step of mounting a needle in the front of the elongated body portion of the needle holder in communication with the fluid path after the needle holder is installed in the nose.

26. The method of claim 24 further including the step of installing the front portion of the plunger assembly into the barrel through the open back end.

27. The method of claim 24 further including the steps of providing a dislodgeable stopper for said retraction cavity and installing it therein.

28. The method of claim 27 wherein said stopper is installed through an opening in the back portion of the plunger assembly.

29. The method of claim 28 wherein the step of installing said stopper includes the step of positioning a portion of said stopper behind and a portion of said stopper beyond the leading end of the plunger head.

30. The method of claim 28 further including sealing the back portion of the plunger assembly after the stopper is installed.

31. The method of claim 30 further including the step of installing the front portion of the plunger assembly into the barrel through the open back end.

32. The method of claim 24 wherein the step of installing the needle holder in the nose portion includes the step of grounding the needle holder to prevent forward movement of the needle holder relative to the nose after installation.

33. The method of claim 32 wherein the needle holder is provided with a tip in front of the elongated body portion and the step of grounding the needle holder in the nose includes the step of causing the tip to project beyond the nose.

34. The method of claim 33 further including the step of mounting the needle in said tip of the needle holder in communication with the fluid path.

35. The method of claim 24 wherein the nose has a wall defining an internal cavity which closely confines the spring and needle holder combination and the step of positioning at least the forward portion of the spring includes the step of using this cavity as a guide to steer the needle holder and uncompressed spring into a compressed state of the spring.

36. A method of assembling a tamperproof retractable syringe which is well suited for automated assembly;

providing a one piece hollow syringe body having a longitudinally extending wall with an open back end, comprising an elongated barrel and nose portion of reduced cross sectional area relative to the barrel, and an inwardly facing surface in the wall at the most constricted part of a transition zone between the barrel and nose where the nose begins;

providing a needle holder having a fluid path, the needle holder having an elongated body portion in front and a head end in back, and providing a spring under the head end which circumscribes the needle holder;

providing a separable retainer member surrounding the head end of the retainer member sealingly and releaseably coupling the retainer member and said head end with a holding force sufficient to resist a retraction force provided to the needle holder by a compressed spring, the retainer member having an outwardly facing surface configured to slidingly and frictionally engage said inwardly facing surface in the nose and hold the needle holder against the retraction force when the spring is compressed within the nose;

loading the spring followed by the needle holder into the back opening in the barrel part of the syringe body and positioning at least the forward portion of the spring and a portion of the elongated body of the needle holder within the nose;

moving the head end of the needle holder and the coupled retainer member into the most constricted part of the transition zone where the nose begins; and installing the coupled needle holder and retainer member in the nose by sliding engagement of the outwardly facing surface of the retainer member with the inwardly facing surface in the wall while compressing the spring within the nose.

* * * * *